(12) United States Patent
Mai et al.

(10) Patent No.: US 6,821,796 B1
(45) Date of Patent: Nov. 23, 2004

(54) METHOD AND SYSTEM FOR TEMPERATURE CYCLING AT AN INTERFACE BETWEEN AN IC DIE AND AN UNDERFILL MATERIAL

(75) Inventors: Zhihong Mai, Singapore (SG); Jiann Min Chin, Singapore (SG); Lihong Cao, Singapore (SG)

(73) Assignee: Advanced Micro Devices, Inc., Sunnyvale, CA (US)

( * ) Notice: Subject to any disclaimer, the term of this patent is extended or adjusted under 35 U.S.C. 154(b) by 49 days.

(21) Appl. No.: 10/199,237

(22) Filed: Jul. 19, 2002

(51) Int. Cl.[7] .................. H01L 21/66; G01R 31/02; G01N 25/00
(52) U.S. Cl. .................. 438/15; 438/14; 438/795; 374/45; 324/755
(58) Field of Search .................. 438/15, 14, 795; 374/45; 324/755

(56) References Cited

U.S. PATENT DOCUMENTS

| | | | |
|---|---|---|---|
| 5,252,834 A | * 10/1993 | Lin | 250/458.1 |
| 5,327,075 A | * 7/1994 | Hashinaga et al. | 324/158.1 |
| 5,422,498 A | * 6/1995 | Nikawa et al. | 257/48 |
| 6,381,356 B1 | * 4/2002 | Murakami et al. | 382/141 |
| 6,488,405 B1 | * 12/2002 | Eppes et al. | 374/5 |

* cited by examiner

Primary Examiner—Michael Trinh
(74) Attorney, Agent, or Firm—Monica H. Choi

(57) ABSTRACT

For temperature cycling at a material of an IC (integrated circuit) package, a laser beam is directed to the material such that the material absorbs the laser beam to become heated. A laser controller adjusts at least one property of the laser beam until the temperature of the material reaches a predetermined high-end temperature. The present invention may be used for a flip-chip IC package with the laser beam being directed toward a back-side of an IC die that is exposed on the IC package. In that case, the laser beam is comprised of light having a wavelength that is within a transmission region of a semiconductor material of the IC die such that the laser beam reaches the material on the front side of the IC die.

18 Claims, 4 Drawing Sheets

METHOD AND SYSTEM FOR TEMPERATURE CYCLING AT AN INTERFACE BETWEEN AN IC DIE AND AN UNDERFILL MATERIAL

TECHNICAL FIELD

The present invention relates generally to manufacture of integrated circuit packages, and more particularly, to a method and system for temperature cycling at an interface between an IC (integrated circuit) die and an underfill material of an IC (integrated circuit) package that accurately reflects temperature cycling during operation of the integrated circuit on the IC die.

BACKGROUND OF THE INVENTION

Referring to FIG. 1, an IC (integrated circuit) package 100 is comprised of an IC (integrated circuit) die 102 mounted to an IC (integrated circuit) package housing 104 with an underfill material 106. The IC package 100 provides connection between pins 108 of the IC package 100 to nodes of the integrated circuit fabricated on the IC die 102, as known to one of ordinary skill in the art of electronics. During operation of the integrated circuit on the IC die 102, power is dissipated, and the IC die 102 heats up.

Temperature cycling is performed for assessing the effect of thermal stress on the IC package 100 as the temperature of the IC die 102 varies from a low-end temperature such as −65° Celsius to a high-end temperature such as 150° Celsius. Referring to FIG. 2, in the prior art, to assess the effect of the high-end temperature on the IC package 100, the IC package 100 is placed within a heating chamber 110. A heat source 112 within the heating chamber 110 changes the environmental temperature within the heating chamber 110. Then, the temperature of the whole IC package 100 including the whole IC die 102 within the IC package 100 gradually heats up from being placed within the heating chamber 110. Typically, the whole IC package 100 heats up to the enviromental temperature within the heating chamber 110 after the IC package 100 has been within the heating chamber for several minutes.

Referring to FIG. 3, an enlarged cross sectional view of the IC die 102 includes active device regions 122 fabricated from a front side 124 of the IC die 102. The IC die 102 is comprised of a semiconductor material, such as silicon for example, for fabricating integrated circuit structures therein. The active device regions 122 are typically shallow from the front side 124 of the semiconductor die. For example, the active device regions 122 may be comprised of drain and source junctions of MOSFETs (metal oxide semiconductor field effect transistors) having depths in a range of hundreds of nanometers to micrometers, as known to one of ordinary skill in the art of integrated circuit fabrication.

A back side 126 of the semiconductor die 102 is opposite to the front side 124 of the semiconductor die 102. In addition, an interlevel dielectric material 128, comprised of silicon dioxide ($SiO_2$) for example, is formed on the front side of the semiconductor wafer. The interlevel dielectric material 128 is comprised of the dielectric material through which interconnect structures are formed, and the interlevel dielectric material 128 is also comprised of encapsulating dielectric material, as known to one of ordinary skill in the art of integrated circuit fabrication.

Typically, within an IC package, the front side 124 of the IC die 102 is mounted to the IC package via an underfill material 130, as known to one of ordinary skill in the art of IC package manufacture. The underfill material 130 is comprised of a material for bonding the IC die 102 to the housing of the IC package. The interlevel dielectric material 128 is disposed at the interface between the front side 124 of the IC die 102 and the underfill material 130 of the IC package.

FIG. 4 shows an example IC package named as a "flip-chip" 150, as known to one of ordinary skill in the art of IC package manufacture. In the flip-chip IC package 150, the IC die 102 is mounted to the IC package housing 106 with the underfill material 130. Each of a plurality of pins 152 of the flip chip IC package 150 provides connection to a respective node of the integrated circuit on the IC die 102 via a respective one of a grid array of contact balls 125. In the flip-chip IC package 150, the front-side 124 of the IC die 102 is mounted to the underfill material 130 while the back side 126 of the IC die 102 is exposed. Referring to FIGS. 3 and 4, an interlevel dielectric material is formed on the front side of the IC die 102 mounted on the flip-chip IC package 150 (similar to the interlevel dielectric material 128 of FIG. 3), and such an interlevel dielectric material 128 is at the interface between the front-side 124 of the IC die 102 and the underfill material 130 of the flip-chip IC package 150.

Further referring to FIGS. 3 and 4, during operation of the integrated circuit on the IC die 102, the front-side 124 of the IC die heats up rapidly as power is dissipated within the active device regions 122 during operation of the integrated circuit on the IC die 102. In addition, the power dissipated through such active device regions 122 is dramatically increasing as the clocking speed of integrated circuits, such as for microprocessors for example, is increasing with technological advancement. Thus, for many modem integrated circuits fabricated on the IC die 102, the front-side 124 of the IC die 102 heats up rapidly, such as in seconds or in less than a second, during operation of the integrated circuit on the IC die 102.

In addition, such rapid heating of the front-side 124 from operation of the integrated circuit on the IC die 102 is localized to the interface between the front side 124 of the IC die 102 and the underfill material 130. The underfill material 130 is typically comprised of a material such as epoxy which is not a good heat conductor. The interlevel dielectric material 128 absorbs the heat generated at the active device regions 122 of the front-side 124 of the IC die 102. Thus, the interface between the front side 124 of the IC die 102 and the underfill material 130 including the interlevel dielectric material 128 heats up rapidly from operation of the integrated circuit on the IC die 102.

Such rapid heating at the interface between the front side 124 of the IC die 102 and the underfill material 130 including the interlevel dielectric material 128 causes thermal stress at such an interface. For example, with such thermal stress, the underfill material 130 may undesirably delaminate from the IC die 102 such that the IC die 102 is not securely mounted to the IC package. It is desired to assess the effect of such thermal stress from the rapid heating localized at the interface between the front side 124 of the IC die 102 and the underfill material 130 including the interlevel dielectric material 128 from operation of the integrated circuit on the IC die 102.

However, the prior art mechanism of temperature cycling to the high-end temperature within the heating chamber 110 of FIG. 2 does not accurately simulate such rapid heating localized at the interface between the front side 124 of the IC die 102 and the underfill material 130 including the interlevel dielectric material 128 from operation of the integrated circuit on the IC die 102. With the heating chamber 110 of FIG. 2 in the prior art, the whole IC package 100 is heated inward from the temperature gradient of the heated environmental temperature within the heating chamber 110. Thus, the heating is not localized to the interface between the front side 124 of the IC die 102 and the underfill material 130 including the interlevel dielectric material 128. In addition, such heating of the IC package 100 within the heating chamber 110 of FIG. 2 in the prior art is gradual over a time period of minutes. Thus, heating is not rapid over a time period of seconds or less than a second.

Thus, a temperature cycling mechanism is desired for more accurately simulating the rapid heating localized at the interface between the front side 124 of the IC die 102 and the underfill material 130 including the interlevel dielectric material 128 from operation of the integrated circuit on the IC die 102.

SUMMARY OF THE INVENTION

Accordingly, in a general aspect of the present invention, a temperature cycling mechanism uses laser energy for more accurately simulating the rapid heating localized at the interface between the front side of the IC die and the underfill material of the IC package including the interlevel dielectric material at the front side of the IC die, from operation of the integrated circuit on the IC die.

In one embodiment of the present invention, in a method and system for temperature cycling at an interface between a front side of an IC (integrated circuit) die and an underfill material of an IC (integrated circuit) package, a front face of the IC die has an interlevel material thereon, and the interlevel material is at the interface between the IC die and the underfill material. A laser source generates a laser beam, and the laser beam is directed from the laser source to the interlevel material such that the interlevel material absorbs the laser beam to become heated from the absorption of the laser beam. A thermometer measures a temperature of the interlevel material. A laser controller is used for adjusting at least one of a pulse duration and a pulse repetition rate of the laser beam until the temperature of the interlevel material reaches a predetermined high-end temperature.

The present invention may be used to particular advantage when the IC package is a flip-chip such that the laser beam is directed toward a back-side of the IC die mounted on the IC package with the back-side of the IC die being exposed. In that case, the laser beam is comprised of a light having a wavelength that is within a transmission region of a semiconductor material of the IC die such that the laser beam is substantially transmitted through the semiconductor material of the IC die to reach the interlevel material on the front side of the IC die.

In an example embodiment, the semiconductor material of the IC die is comprised of silicon having the transmission region for wavelength of light being in a range of from about 1 $\mu$m (micrometer) to about 20 $\mu$m (micrometer). In that case, the laser beam is from a $CO_2$ laser source for generating light having a wavelength of about 10.6 $\mu$m (micrometer). The laser beam applied on the back-side of the IC die has a power of about 15 Watts, a pulse duration of about 100 $\mu$s (microsecond), and a pulse repetition rate of about 1 Kilo-Hertz, for generating the predetermined high-end temperature of about 150° Celsius at the interlevel material comprised of silicon dioxide.

In another embodiment of the present invention, the laser beam is applied toward the back-side of the IC die for a predetermined time period, and a microscopy image of the interface between the front side of the IC die and the underfill material of the IC package is generated for detecting delamination of the underfill material from the IC die resulting from the temperature cycling.

In this manner, laser energy is applied and absorbed at a localized area (i.e., the interlevel dielectric material at the interface between the front side of the IC die and the underfill material of the IC package). In addition, with application of the laser beam to the localized area, the temperature of such a localized area heats up rapidly over a time period of seconds or less than a second. Thus, the temperature cycling mechanism of the present invention more accurately simulates the rapid heating localized at the interface between the front side of the IC die and the underfill material of the IC package including the interlevel dielectric material at the front side of the IC die from operation of the integrated circuit on the IC die.

These and other features and advantages of the present invention will be better understood by considering the following detailed description of the invention which is presented with the attached drawings.

BRIEF DESCRIPTION OF THE DRAWINGS

The figures referred to herein are drawn for clarity of illustration and are not necessarily drawn to scale. Elements having the same reference number in FIGS. 1–8 refer to elements having similar structure and function.

DETAILED DESCRIPTION

Figure 5:
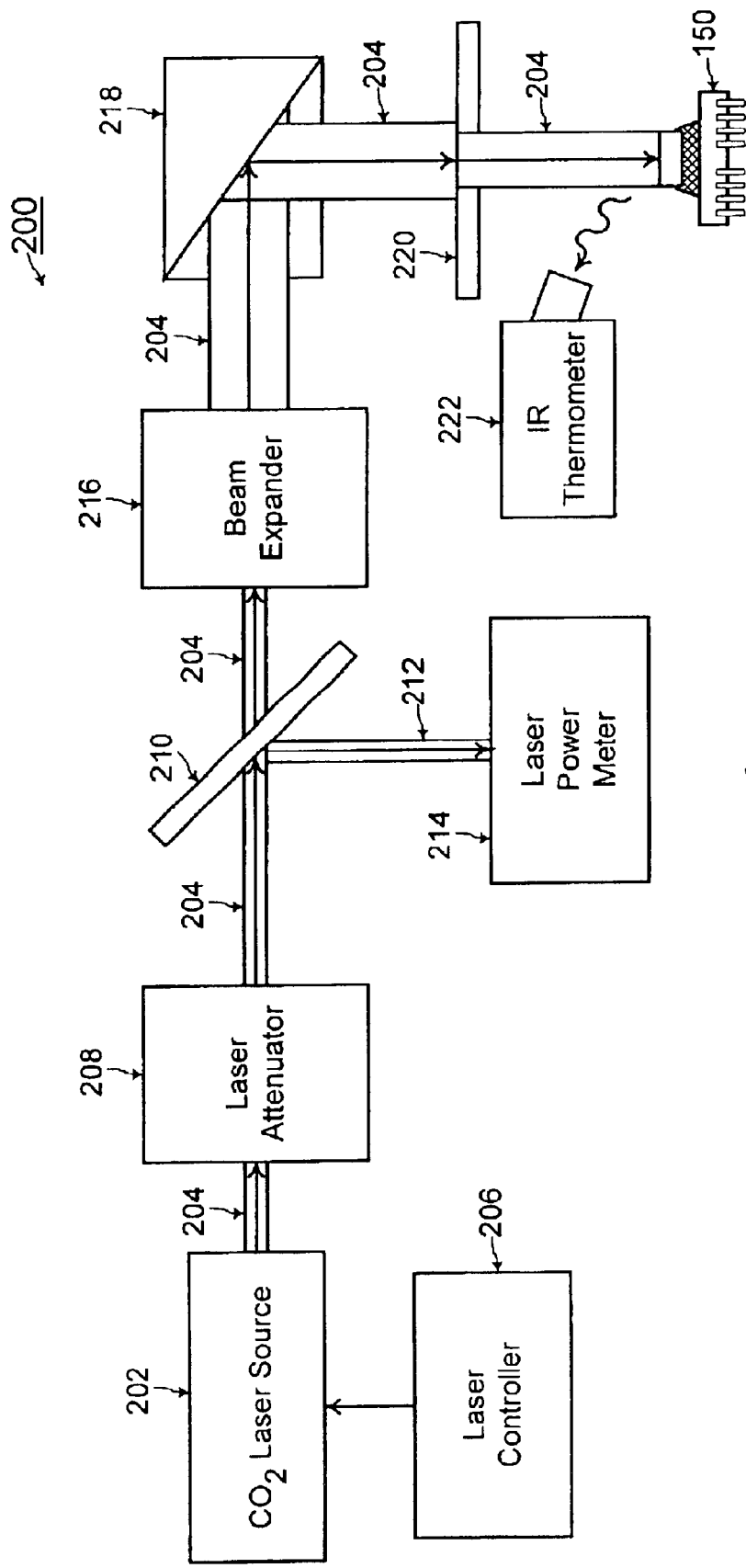
FIG. 5 shows components of a system for using laser energy in temperature cycling that more accurately simulates the rapid heating localized at the interface between the front side of the IC die and the underfill material of the IC package including the interlevel dielectric material at the front side of the IC die, from operation of the integrated circuit on the IC die, according to an embodiment of the present invention.

Referring to FIG. 5, a temperature cycling system 200 of an embodiment of the present invention includes a laser source 202 for generating a laser beam 204. The laser beam 204 according to one embodiment of the present invention is generated in pulse mode with a cycle of laser pulses having a pulse repetition rate and a pulse duration. A laser controller 206 controls the laser source 202 for adjusting the pulse repetition rate and the pulse duration of the laser pulses generated by the laser source 202. Such a laser source 202 and such a laser controller 206 are individually known to one of ordinary skill in the art of lasers and electronics.

In addition, the laser beam 204 from the laser source 202 is passed through a laser attenuator 208 for adjusting the power of the laser beam 204. The power of the laser beam 204 after going through the laser attenuator 208 is usually less than the power of the laser beam 204 from the laser source 202. The laser beam 204 from the laser attenuator 208 is sampled with a beam sampler 210. The beam sampler 210 lets through most of the energy of the laser beam 204 from the laser attenuator 208 but also directs a relatively small energy portion of the laser beam 212 from the laser attenuator 208 to a laser power meter 214. The laser power meter 214 together with the beam sampler 210 determine the power of the laser beam 204 from the laser attenuator 208. The laser attenuator 208, the beam sampler 210, and the laser power meter 214 are individually known to one of ordinary skill in the art of lasers and electronics.

Furthermore, the laser beam 204 that passes through the beam sampler 210 further travels through a beam expander 216. The beam expander 216 expands the area of illumination of the laser beam 204 and more uniformly distributes the energy of the laser beam 204 throughout such an illuminated area. Such a beam expander 216 individually is known to one of ordinary skill in the art of lasers and electronics.

Additionally, the laser beam 204 from the beam expander 216 is redirected with a mirror 218 toward an aperture 220. The aperture 220 includes an opening for defining an area of illumination of the laser beam 204 at the IC package 150 under test. Such a mirror 218 and such an aperture 220 are individually known to one of ordinary skill in the art of lasers and electronics.

Figure 1:
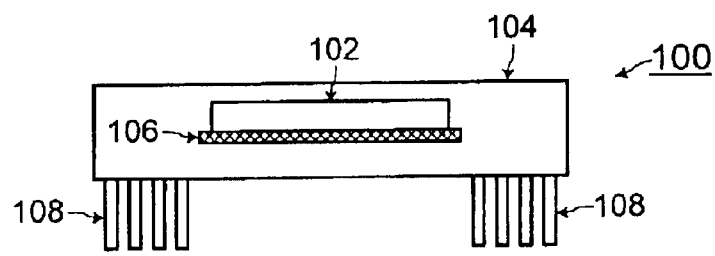
FIG. 1 shows an example of an IC die mounted to an IC package, according to the prior art.
Figure 2:
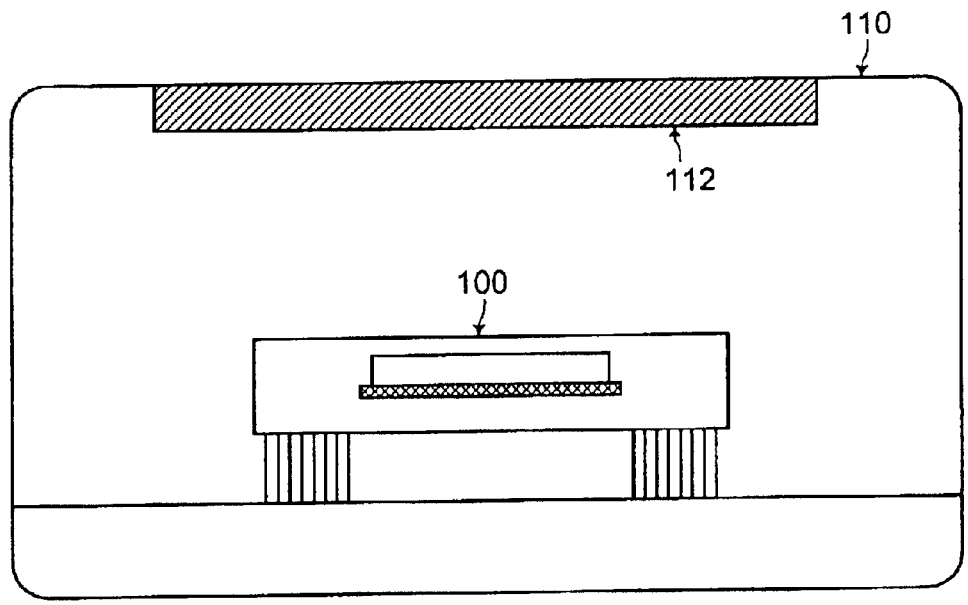
FIG. 2 shows a heating chamber for temperature cycling the IC package to a high end temperature, according to the prior art.
Figure 3:
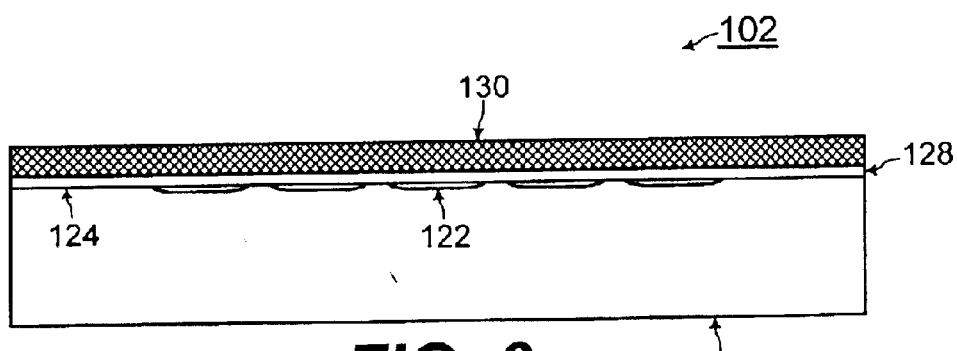
FIG. 3 shows an enlarged cross sectional view of the IC die including active device regions formed on a front-side of the IC die that also interfaces with an underfill material of the IC package.
Figure 4:
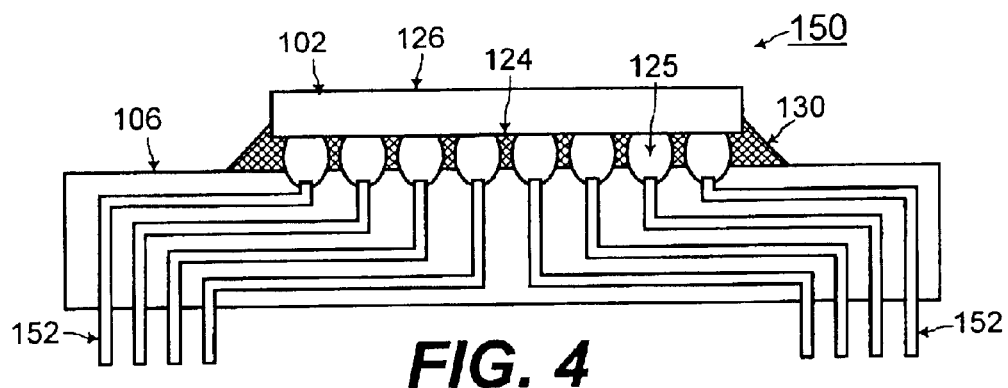
FIG. 4 shows components of a "flip-chip" IC package with the back side of the IC die exposed and with the front side of the IC die interfacing with the underfill material of the flip-chip IC package.
Figure 6:
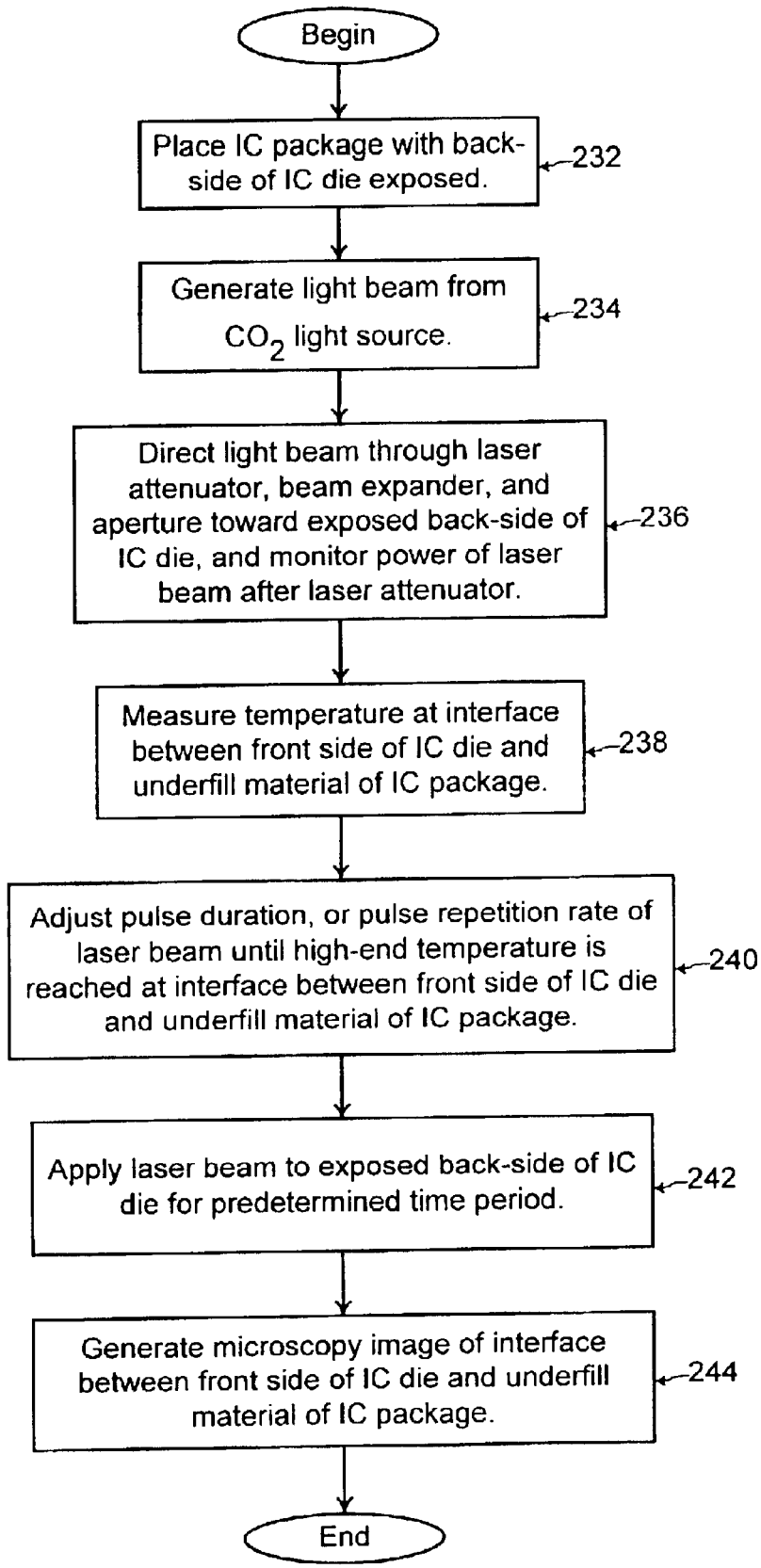
FIG. 6 shows a flow-chart of steps during operation of the system of FIG. 5, according to an embodiment of the present invention.

FIG. 6 shows a flow-chart of operation of the temperature cycling system 200 of FIG. 5. Referring to FIGS. 4 and 5, the flip-chip IC package 150 is placed in the path of the laser beam 204 from the aperture 220 (step 232 of FIG. 6). In addition, the exposed back-side 126 of the IC die 102 mounted on the flip-chip IC package 150 is placed to face toward the laser beam 204 from the aperture 220 (step 232 of FIG. 6). After such placement of the flip-chip IC package 150, the light beam is generated from the laser source 202 (step 234 of FIG. 6) and directed to reach the back side 126 of the flip-chip IC package 150 (step 236 of FIG. 6).

Figure 7:
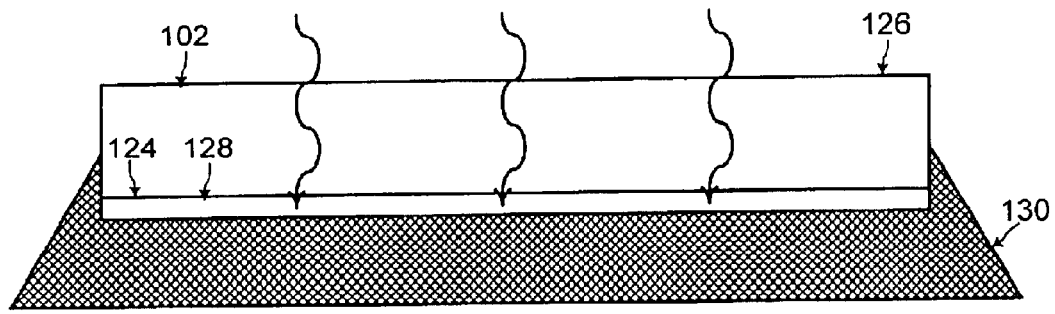
FIG. 7 shows an enlarged cross sectional view illustrating transmission of the laser beam through the exposed back side of the IC die to reach the interlevel material at the interface between the front side of the IC die and the underfill material of the IC package within the system of FIG. 5, according to an embodiment of the present invention.

FIG. 7 shows an enlarged view of the front side 124 of the IC die 102 interfacing with the underfill material 130 of the IC package 150 with the interlevel dielectric material 128 at such an interface. In one embodiment of the present invention, the IC die 102 is comprised of a semiconductor material such as silicon for example. The semiconductor material of the IC die 102 has a laser transmission region. Any light having a wavelength within the range of the laser transmission region of the semiconductor material of the IC die 102 is transmitted through the semiconductor material of the IC die 102. For example, when the semiconductor material of the IC die 102 is silicon, the laser transmission region for silicon is in a range of from about 1 $\mu$m (micrometer) to about 20 $\mu$m (micrometer). Thus, a laser light having a wavelength in the range of from about 1 $\mu$m (micrometer) to about 20 $\mu$m (micrometer) is substantially transmitted through silicon.

Referring to FIGS. 5 and 7, the laser source 202 is a $CO_2$ laser source for generating the laser beam 204 comprised of light having a wavelength of about 10.6 $\mu$m (micrometer). Such a laser beam 204 from the $CO_2$ laser source has light with the wavelength being within the range of the transmission region for silicon of the IC die 102. Thus, in that case, referring to FIG. 7, the light of the laser beam 204 is substantially transmitted through the silicon of the IC die 102 to reach the interlevel dielectric material 128 (as illustrated by the wavy arrowed lines in FIG. 7).

The interlevel dielectric material 128 that is comprised of silicon dioxide ($SiO_2$) and that is disposed at the interface between the front side 124 of the IC die 102 and the underfill material 130 absorbs the light of the laser beam 204 that reaches the interlevel dielectric material 128 and heats up. Referring to FIG. 5, the temperature of the interlevel dielectric material 128 is measured with an IR (infra-read) thermometer 222 (step 238 of FIG. 6). The IR (infra-read) thermometer 222 is directed toward the back-side of the IC die 102 of the flip-chip IC package 150 and measures the irradiation emanating from the backside 126 of the IC die 102. Such irradiation emanating from the back-side of the IC die 102 of the flip-chip IC package 150 is from heating at the interlevel dielectric material 128. The IR (infra-read) thermometer 222 determines the temperature of the interlevel dielectric material 128 at the interface between the front side 124 of the IC die 102 and the underfill material 130 from measuring such irradiation emanating from the back-side 126 of the IC die 102 of the flip-chip IC package 150. Such an IR (infra-read) thermometer 222 individually is known to one of ordinary skill in the art of lasers and electronics.

The laser controller 206 is used to adjust the pulse repetition rate and the pulse duration of the laser pulses of the laser beam 204 from the $CO_2$ laser source until the temperature at the interlevel dielectric material 128 as measured by the IR (infra-read) thermometer 222 reaches a predetermined high-end temperature (step 240 of FIG. 6). The predetermined high-end temperature is 150° Celsius according to one embodiment of the present invention. In addition, the laser attenuator 208 is used to adjust the power of the laser beam 204 from the laser attenuator 208 as measured by the laser power meter 214.

In one embodiment of the present invention, the laser beam 204 from the $CO_2$ laser source having light with the wavelength of 10.6 $\mu$m (micrometer) is generated to have a power of about 15 Watts from the laser attenuator 208 as measured by the laser power meter 212 in FIG. 5. In addition, the laser controller 206 is used to adjust the pulse repetition rate and the pulse duration of the laser pulses of the laser beam 204 from the $CO_2$ laser source to be about 1 Kilo-Hertz and about 100 $\mu$s (microsecond), respectively. With such a laser beam 204, the high end temperature at the interlevel dielectric material 128 as measured by the IR (infra-read) thermometer 222 reaches 150° Celsius.

Figure 8:
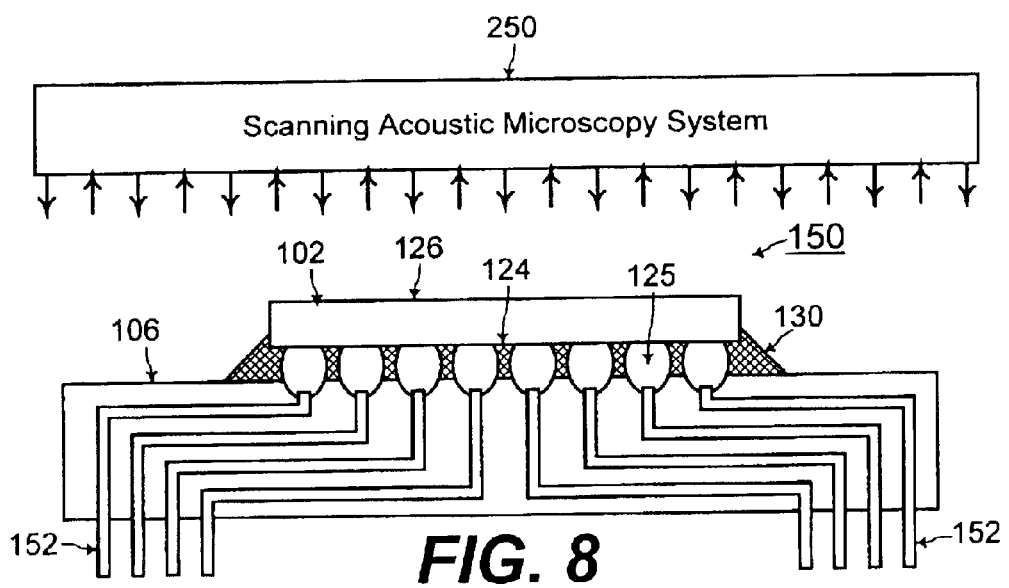
FIG. 8 shows a SAM (scanning acoustic microscopy) system used for generating a microscopy image of the interface between the front side of the IC die and the underfill material of the IC package after heating within the system of FIG. 5, according to an embodiment of the present invention.

Such a laser beam 204 is applied to the exposed back side 126 of the IC die 102 of the flip-chip IC package 150 for a predetermined time period, such as for about 15 minutes for example (step 242 of FIG. 6). Then, referring to FIG. 8, after such a time period of temperature cycling stress, a microscopy image of the interface between the front side 124 of the IC die 102 and the underfill material 130 is generated with a microcopy system 250 (step 244 of FIG. 6). The microscopy system 250 is a SAM (scanning acoustic microscopy) system according to one embodiment of the present invention. Such a SAM (scanning acoustic microscopy) system 250 penetrates acoustic waves below the surface of the IC package 150 to generate a microscopy image of the interface between the front side 124 of the IC die 102 and the underfill material 130. Such a microscopy image shows any delamination of the underfill material 130 of the IC package 150 from the IC die 102. Such a SAM (scanning acoustic microscopy) system 250 individually is known to one of ordinary skill in the art of lasers and electronics.

In this manner, laser energy is applied and absorbed at a localized area (i.e., the interlevel dielectric material 128 at the interface between the front side 124 of the IC die 102 and the underfill material 130 of the IC package 150). In addition, with application of the laser beam to the localized area, the temperature of such a localized area heats up rapidly over a time period of seconds or less than a second. Thus, the temperature cycling mechanism of the present invention more accurately simulates the rapid heating localized at the interface between the front side 124 of the IC die 102 and the underfill material 130 of the IC, package 150 including the interlevel dielectric material 128 at the front side 124 of the IC die 102 from operation of the integrated circuit on front side 124 of the IC die 102.

The foregoing is by way of example only and is not intended to be limiting. For example, other types of IC package with other types of IC die may be used with the temperature cycling system 200 of the present invention. For instance, the semiconductor material of the IC die may be different from silicon with a different light wavelength transmission range. Furthermore, as will be understood by those skilled in the art, the structures described herein may be made or used in the same way regardless of their position and orientation. Accordingly, it is to be understood that terms and phrases such as "front" and "back" as used herein refer to relative location and orientation of various portions of the structures with respect to one another, and are not intended to suggest that any particular absolute orientation with respect to external objects is necessary or required.

The present invention is limited only as defined in the following claims and equivalents thereof.

We claim:

1. A method of temperature cycling at a heated material of an IC (integrated circuit) package, including the steps of:

directing a laser beam to the heated material through another material of the IC package such that the heated material absorbs the laser beam to become heated;

wherein the laser beam is substantially transmitted through the another material before reaching the heated material;

measuring a temperature of the heated material; and adjusting at least one property of the laser beam until the temperature of the heated material reaches a predetermined high-end temperature.

2. The method of claim 1, wherein the adjusted property of the laser beam includes at least one of a pulse duration and a pulse repetition rate of the laser beam.

3. The method of claim 1, wherein the heated material is an interlevel dielectric material disposed between a front side of an IC die and an underfill material of the IC package.

4. The method of claim 1, further including the steps of:

passing the laser beam from a laser source through a laser attenuator for controlling power of the laser beam;

passing the laser beam from the attenuator through a beam expander; and passing an area portion of the laser beam from the beam expander through an aperture to an area of the IC package.

5. The method of claim 4, further including the step of:

monitoring the power of the laser bean by sampling a reflection of an energy portion of the laser beam from the attenuator.

6. The method of claim 1, wherein the another material is a back-side of the IC die.

7. The method of claim 6, wherein the back-side of the IC die is comprised of silicon.

8. The method of claim 7, wherein the laser beam is from a $CO_2$ laser source for generating light having a wavelength of about 10.6 $\mu$m (micrometer).

9. The method of claim 1, wherein the laser beam has a wavelength within a transmission region of the another material such that the laser beam is substantially transmitted through the another material.

10. A method of temperature cycling at a material of an IC (integated circuit) package, including the steps of:

directing a laser beam to the material of the IC package such that the material absorbs the laser beam to become heated, wherein the material is an interlevel dielectric material disposed between a front side of an IC die and an underfill material of the IC package;

and wherein the laser beam is directed toward a back-side of the IC die that is exposed on the IC package, and wherein the laser beam has a wavelength within a transmission region of a semiconductor material of the IC die such that the laser beam reaches the interlevel dielectric material on the front side of the IC die;

measuring a temperature of the material; and adjusting at least one property of the laser beam until the temperature of the material reaches a predetermined high-end temperature.

11. The method of claim 10, wherein the semiconductor material of the IC die is comprised of silicon having the wavelength transmission region in a range of from about 1 $\mu$m (micrometer) to about 20 $\mu$m (micrometer).

12. The method of claim 11, wherein the laser beam is from a $CO_2$ laser source for generating light having a wavelength of about 10.6 $\mu$m (micrometer).

13. The method of claim 12, wherein the laser beam has a power of about 15 Watts, a pulse duration of about 100 $\mu$s (microsecond), and a pulse repetition rate of about 1 KiloHertz, for generating the predetermined high-end temperature of about 150° Celsius at the interlevel dielectric material comprised of silicon dioxide.

14. The method of claim 13, further including the steps of:

applying the laser beam toward the back-side of the IC die for about 15 minutes; and generating a microscopy image of an interface between the interlevel dielectric material and the underfill material for detecting delamination of the underfill material.

15. The method of claim 10, wherein an IR (infra-red) thermometer is directed toward the back-side of the IC die for measuring irradiation emanating from the back-side of the IC die.

16. The method of claim 3, wherein the another material is a back-side of the IC die.

17. The method of claim 16, wherein the back-side of the IC die is comprised of silicon.

18. The method of claim 17, wherein the laser beam is from a $CO_2$ laser source for generating light having a wavelength of about 10.6 $\mu$m (micrometer).

* * * * *